United States Patent
Cleary

[11] Patent Number: 5,980,247
[45] Date of Patent: Nov. 9, 1999

[54] MANDIBULAR REPOSITIONING DEVICE

[75] Inventor: James D. Cleary, Glendora, Calif.

[73] Assignee: 3M Innovative Properties Company, St. Paul, Minn.

[21] Appl. No.: 09/063,746

[22] Filed: Apr. 21, 1998

[51] Int. Cl.[6] .................................................. A61C 3/00
[52] U.S. Cl. .................................................. 433/19
[58] Field of Search ........................... 433/6, 18, 19, 433/20, 21

[56] References Cited

U.S. PATENT DOCUMENTS

| | | | |
|---|---|---|---|
| 473,040 | 4/1892 | Wilder | 433/18 |
| 934,958 | 9/1909 | Case | 433/7 |
| 3,312,216 | 4/1967 | Wallshein | 433/6 |
| 3,798,773 | 3/1974 | Northcutt | 32/14 E |
| 4,382,783 | 5/1983 | Rosenberg | 433/19 |
| 4,462,800 | 7/1984 | Jones | 433/19 |
| 4,551,095 | 11/1985 | Mason | 433/19 |
| 4,708,646 | 11/1987 | Jasper | 433/19 |
| 4,795,342 | 1/1989 | Jones | 433/19 |
| 4,815,972 | 3/1989 | Howe . | |
| 5,183,388 | 2/1993 | Kumar | 433/19 |
| 5,352,116 | 10/1994 | Wet | 433/19 |
| 5,435,721 | 7/1995 | Vogt | 433/19 |
| 5,562,445 | 10/1996 | De Vincenzo et al. | 433/19 |
| 5,645,423 | 7/1997 | Collins, Jr. | 433/21 |
| 5,645,424 | 7/1997 | Collins, Jr. | 433/21 |
| 5,651,672 | 7/1997 | Cleary et al. | 433/19 |
| 5,678,990 | 10/1997 | Rosenberg | 433/19 |
| 5,711,667 | 1/1998 | Vogt | 433/19 |
| 5,718,576 | 2/1998 | Schnaitter et al. | 433/22 |
| 5,738,514 | 4/1998 | De Vincenzo et al. | 433/19 |
| 5,879,157 | 3/1999 | Scheu | 433/19 |

FOREIGN PATENT DOCUMENTS 2087079A 12/1971 France .

OTHER PUBLICATIONS

Eureka Spring! Clinical Information, Saw Luis Obispo, Calif 93401 updates May 1996, Aug. 1996, Feb. 1997.

*Primary Examiner*—Ralph A. Lewis
*Attorney, Agent, or Firm*—James D. Christoff

[57] ABSTRACT

A device for repositioning the mandibular jaw relative to the maxilliary jaw during orthodontic treatment has two links connected together by a pivot. Each link is also pivotally connected to one of the patient's jaws at a position remote from the pivot. As the jaws are closed, the links urge the relative positions of the jaws to certain orientations as determined by the practitioner.

23 Claims, 6 Drawing Sheets

MANDIBULAR REPOSITIONING DEVICE

BACKGROUND OF THE INVENTION

1. Field of the Invention

This invention relates to a device useful during orthodontic treatment for repositioning the mandibular jaw. More specifically, this invention relates to a mandibular repositioning device for urging the lower jaw either in a forwardly or a rearwardly direction relative to the upper jaw in order to improve occlusion.

2. Description of the Related Art

Orthodontic treatment involves movement of malpositioned teeth to orthodontically correct positions. During treatment, tiny orthodontic appliances known as brackets are often connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to the patient's molar teeth. The brackets, archwires and buccal tubes are commonly referred to as "braces".

The orthodontic treatment of some patients include correction of the alignment of the upper dental arch with the lower dental arch. For example, certain patients have a condition referred to as a Class II malocclusion where the lower dental arch is located an excessive distance in a rearwardly direction relative to the location of the upper dental arch when the jaws are closed. Other patients may have an opposite condition referred to as a Class III malocclusion wherein the lower dental arch is located in a forwardly direction of its desired location relative to the position of the upper dental arch when the jaws are closed.

Orthodontic treatment of Class II and Class III malocclusions are commonly corrected by movement of the upper dental arch as a single unit relative to movement of the lower dental arch as a single unit. To this end, forces are often applied to each dental arch as a unit by applying force to the brackets or buccal tubes, the archwires, or attachments connected to the brackets, buccal tubes, or archwires. In this manner, a Class II or Class III malocclusion can be corrected at the same time that the archwires and the brackets are used to move individual teeth to desired positions relative to each other.

Correction of Class II and Class III malocclusions is sometimes carried out by use of a force-applying system known as headgear that includes strapping which extends around the rear of the patient's head. The strapping is often connected by tension springs that, in turn, are connected to the buccal tubes, the brackets or one of the archwires. Additionally, as an alternative for correction of Class III malocclusions, the strapping may be connected by tension springs to a chin cup that externally engages the patient's chin. In either instance, the strapping and springs serve to apply a rearwardly-directed force to the associated jaw.

However, headgear is often considered unsatisfactory because it is visibly apparent. Headgear may serve as a source of embarrassment, particularly among child and teenage patients who may experience teasing from classmates. The embarrassment can be somewhat reduced if the orthodontist instructs the patient to wear the headgear only at night, but unfortunately such practice may lengthen treatment time since the desired corrective forces are applied during only a portion of each calendar day.

Consequently, many practitioners and patients favor the use of intra-oral devices for correcting Class II and Class III malocclusions. Such devices are often located near the cuspid, bicuspid and molar teeth and away from the patient's anterior teeth. As a result, intra-oral devices for correcting Class II and Class III malocclusions are hidden in substantial part once installed and eliminate much of the patient embarrassment that is often associated with headgear.

Orthodontic force modules made of an elastomeric material have been used in the past to treat Class II and Class III malocclusions by connecting a pair of such force modules between the dental arches on opposite sides of the oral cavity. Elastomeric force modules are often used in tension to pull the jaws together in a direction along references lines that extend between the points of attachment of each force module. Such force modules may be an O-ring or a chain-type module made of a number of integrally connected O-rings. However, these modules are typically removable by the patient for replacement when necessary, since the module may break or the elastomeric material may degrade during use to such an extent that the amount of tension exerted is not sufficient.

Unfortunately, orthodontic devices such as headgear and removable force modules are not entirely satisfactory for use with some patients, because the effectiveness of the devices is dependent upon the patient's cooperation. Neglect of the patient to faithfully wear the headgear each day or install new elastomeric force modules as appropriate can seriously retard the progress of treatment and defeat timely achievement of the goals of an otherwise well-planned treatment program, resulting in an additional expenditure of time for both the patient and the orthodontist.

As a result, a number of intra-oral devices that are non-removable by the patient have been proposed in the past to overcome the problems of patient cooperation associated with headgear and with removable intra-oral force modules. For example, U.S. Pat. Nos. 3,798,773, 4,462,800 and 4,551,095 disclose telescoping tube assemblies that urge the jaws toward positions of improved alignment. The assemblies are securely coupled to other orthodontic appliances such as brackets or buccal tubes by the practitioner, and the problems of patient non-compliance are avoided.

Other orthodontic devices for correcting Class II and Class III malocclusions are described in U.S. Pat. Nos. 4,708,646, 5,352,116, 5,435,721 and 5,651,672. The devices described in these references include flexible members that are connected to upper and lower jaws of a patient. The length of the members is selected such that the member is curved in an arc when the patient's jaws are closed. The members have an inherent bias that tends to urge the members toward a normally straight orientation to provide a force that pushes one jaw forwardly or rearwardly relative to the other jaw when the jaws are closed.

U.S. Pat. Nos. 5,645,424 and 5,678,990 describe intra-oral devices for correcting Class II and Class III malocclusions having linkage that includes pivotal connections. The devices in both of these references have a somewhat overall "Z" shaped configuration. A device having a somewhat similar overall configuration is shown in U.S. Pat. No. 5,645,423 and includes double helical loops located on each side of a central segment.

The intra-oral devices described in the aforementioned U.S. Pat. Nos. 5,645,423, 5,645,424 and 5,678,990 have outer arms or shanks for connection to respective tubes. One of the tubes is connected to a molar tooth of the patient's upper dental arch and the other tube is coupled to a molar tooth of the patient's lower dental arch. It is an advantage to connect such intra-oral devices to the molar teeth of both arches, because the relatively large size of the roots of the molar teeth provides a good anchoring location for applying forces to move one jaw relative to the other jaw.

Although a variety of devices for correcting Class II and Class III malocclusions have been suggested in the past as noted above, there is a continued need in the art to improve existing options and to provide new devices that represent alternatives for treatment. Preferably, such new alternatives would function reliably and efficiently so treatment time is not lengthened, yet also be of simplified construction that would not be prone to breakage or cause difficulties during its manufacture.

SUMMARY OF THE INVENTION

The present invention is related in one aspect to a mandibular repositioning device that comprises an upper link having a mesial end portion and a distal end portion, and a lower link having a mesial end portion and a distal end portion. A pivot connects the mesial end portion of the upper link to the mesial end portion of the lower link. An upper connector is pivotally coupled to the distal end portion of the upper link, and a lower connector is pivotally coupled to the distal end portion of the lower link. The upper connector and the lower connector each have a configuration for partial reception into passages of an upper molar appliance and a lower molar appliance respectively. The upper link and the lower link each have a length sufficient to urge one jaw forward relative to the other jaw when the jaws are closed.

In another aspect, the present invention is directed toward a mandibular repositioning device that consists essentially of an upper link, and upper connector pivotally connected to the upper link for coupling the upper link to an appliance fixed to a tooth of the patient's upper jaw, a lower link, a lower connector pivotally coupled to the lower link for coupling the lower link to an appliance fixed to a molar tooth of the patient's lower jaw, and a pivot interconnecting the upper link and the lower link. The pivot is remote from the upper connector and the lower connector.

The invention is also directed toward an orthodontic treatment assembly that includes an upper orthodontic appliance secured to one or more teeth of the patient's upper dental arch and a lower orthodontic appliance secured to one or more teeth of the patient's lower dental arch. The assembly also includes a mandibular repositioning device having an upper link, a lower link and a pivot interconnecting the upper link and the lower link. The upper link is pivotally connected to the upper appliance and the lower link is pivotally connected to the lower appliance.

The invention also concerns an orthodontic treatment assembly that includes an upper orthodontic appliance secured to an upper molar tooth and a lower orthodontic appliance secured to a lower molar tooth. The assembly also has a mandibular repositioning device having an upper link pivotally connected to the upper appliance and a lower link pivotally connected to the lower appliance. The upper link has a mesial end portion, and the lower link has a mesial end portion that is pivotally connected to the mesial end portion of the upper link.

The present invention in its various aspects is an advantage, in that it represents a simplified construction over known mandibular repositioning devices or orthodontic assemblies having linkages of one form or another. Such simplified construction reduces the possibility that the device will be damaged or break during the course of orthodontic treatment.

These and other aspects of the invention are described in more detail in the text that follows and are illustrated in the accompanying drawings.

BRIEF DESCRIPTION OF THE DRAWINGS

FIG. 5b is an end cross-sectional view of the connector depicted in FIG. 5a;

DETAILED DESCRIPTION OF THE PREFERRED EMBODIMENTS

A mandibular repositioning device constructed in accordance with one embodiment of the present invention is illustrated in FIGS. 1–7 and is designated broadly by the numeral 10. The device 10 has two linkages consisting of an upper link 12 and a lower link 14. Each of the links 12, 14 has a mesial (i.e., extending in a direction toward the center of the dental arch) end portion and a distal (i.e., extending in a direction away from the center of the dental arch) end portion.

A central pivot 16 connects the mesial end portion of the upper link 12 to the mesial end portion of the lower link 14. In the embodiment illustrated in FIGS. 1–3, and as shown in more detail in FIG. 4, the pivot 16 includes a shank 11 that extends through holes of the mesial end portion of the upper link 12 and the lower link 14. The pivot 16 preferably has an enlarged, circular cap or head 13 on one end that faces the patient's cheeks. Once the shank 11 is inserted into the holes, the remaining end is peened over in a forming operation to create a second enlarged head 15. Preferably, the pivot 16 includes a semi-cylindrical section 17, and the head 15 extends through and retains a tooth-facing circular cover 19 snugly against the section 17. (In FIG. 3, the head 13 has been shown in dashed lines to reveal inner details of the pivot 16).

The pivot 16 may alternatively comprise other types of constructions as well. For example, the mesial end portion of one of the links 12, 14 may lack the aforementioned hole and instead be integrally connected to a pin that extends transversely of that link's longitudinal axis. The pin in turn is inserted through a hole in the mesial end portion of the other link 12, 14, and peened over in a forming operation to provide a pivotal connection. As another example, the pivot 16 may comprise a machine screw and threaded nut which optionally may be disconnected for separation of the links 12, 14 when desired. Other types of pivots may also be employed.

An upper pivotal connector 18 is pivotally coupled to the distal end portion of the upper link 12. The upper connector 18 is shown in enlarged top view in FIG. 5 and preferably is made of a section of stiff, cylindrical wire that is bent initially to a somewhat "L"-shaped configuration presenting a mesial section 21 and a distal section. The distal section of the connector 18 extends through a hole of the distal end portion of the upper link 12, and includes an outer enlarged head 20 somewhat larger than the hole. The mesial section 21 of the upper connector 18 has a shape adapted to be received in a tubular opening of a buccal tube or other appliance affixed to a tooth of the patient's upper jaw. The connector 18 may be formed by bending an orthodontic pin if desired.

Figure 1:
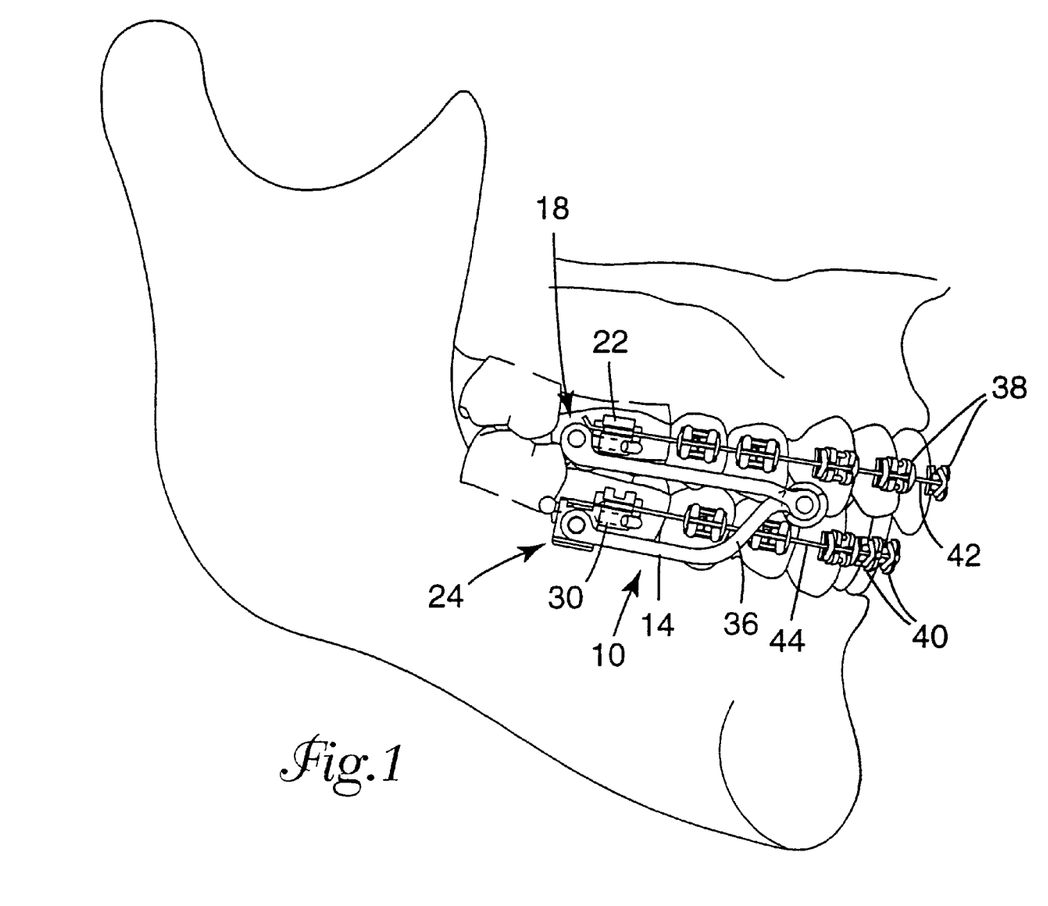
FIG. 1 is a schematic side view of an upper and lower dental arch of a patient undergoing orthodontic treatment, wherein a mandibular repositioning device according to one embodiment of the present invention is illustrated.
Figure 2:
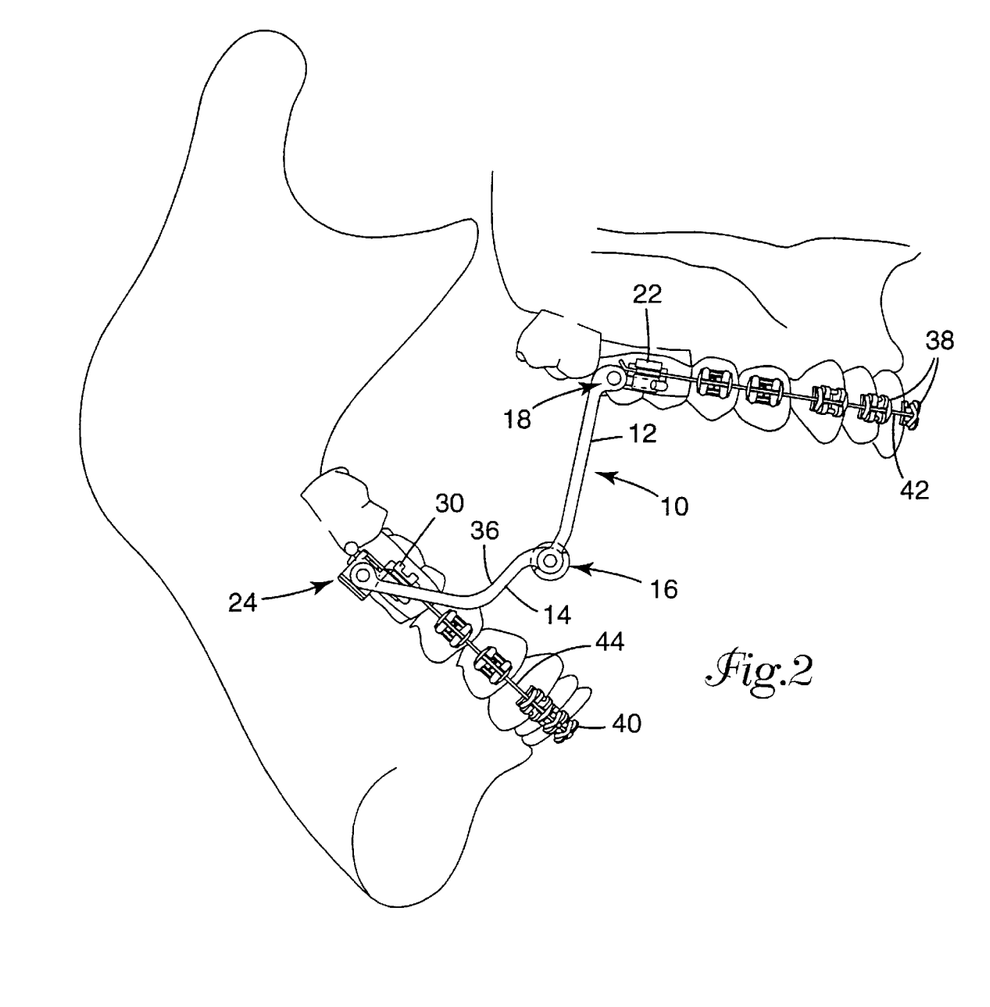
FIG. 2 is a view somewhat similar to FIG. 1 except that the patient's jaws have been opened.
Figure 3:
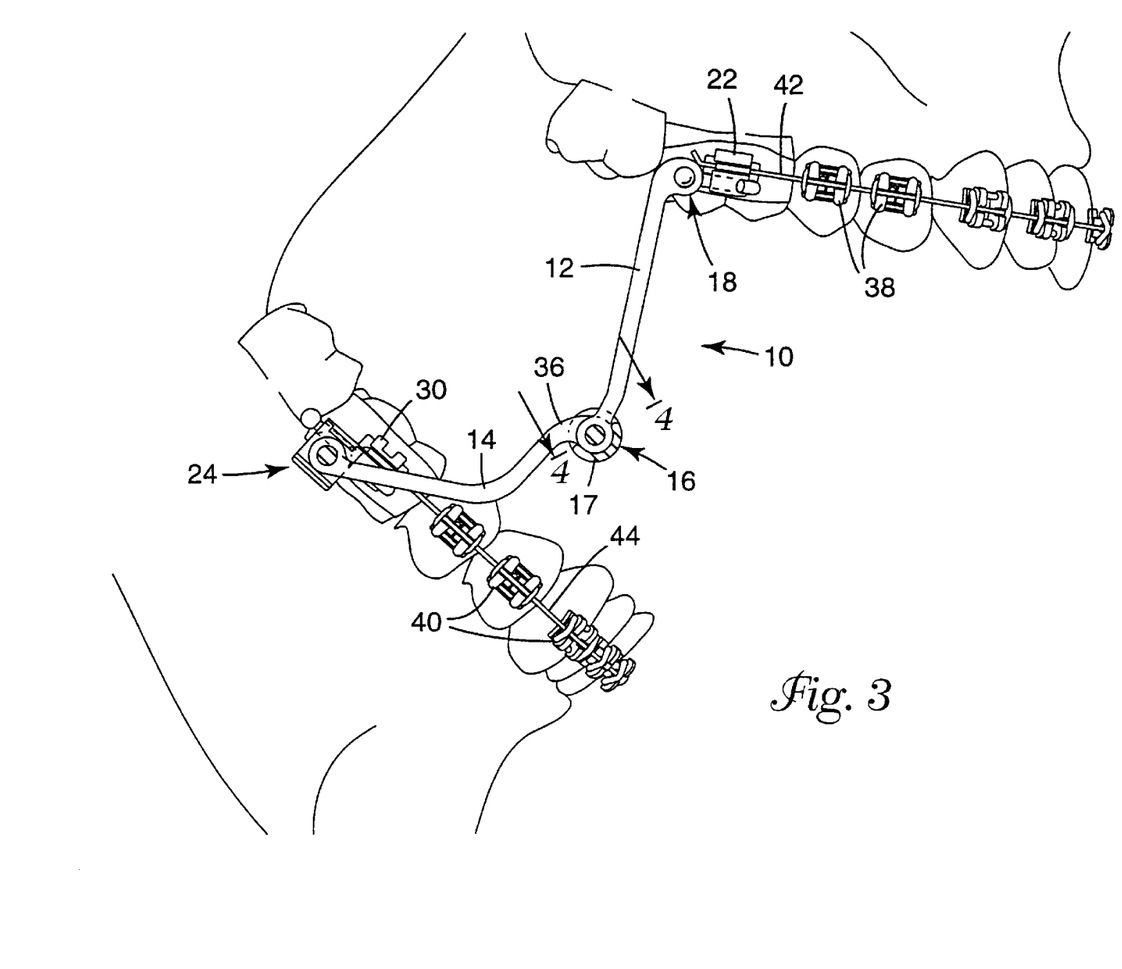
FIG. 3 is an enlarged side view of a portion of FIG. 2.
Figure 4:
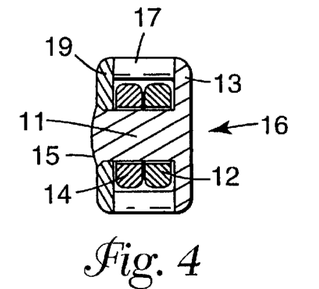
FIG. 4 is an enlarged end cross-sectional view of a central pivot of the mandibular repositioning device.

In FIGS. 1–3, the mesial section 21 of the upper connector 18 extends in a mesial-distal direction through a tubular opening of a headgear tube or buccal tube 22. The buccal tube 22, in turn, is fixed to an orthodontic band that extends around and is connected to a first molar tooth located on the upper jaw of the orthodontic patient. Alternatively, however, the mesial section 21 of the upper connector 18 can be coupled to other types of appliances that are preferably, but not necessarily, connected to one of the patient's molar teeth of the upper jaw. Other types of appliances include brackets, buttons, archwires, or auxiliary archwires, or a cantilever device such as is described in U.S. Pat. No. 5,718,576.

Figure 5:
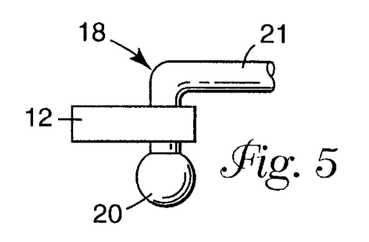
FIG. 5 is an enlarged fragmentary plan view of an upper pivotal connector of the device shown in FIG. 1–3.
Figure 5A:
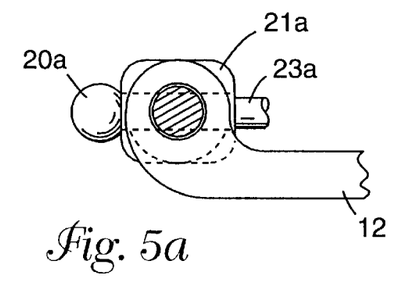
FIG. 5a is an enlarged fragmentary side view in partial section illustrating an alternative upper pivotal connector of the device shown in FIGS. 1–3.
Figure 5B:
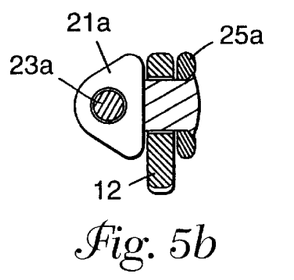

An alternative upper pivotal connector 18a is shown in FIGS. 5a and 5b and includes a body 21a having a hole through which a pin 23a extends. The pin 23a includes an enlarged spherical head 20a as well as a shaft that extends in a mesial direction through a tubular opening of a headgear tube or a buccal tube (such as the buccal tube 22 depicted in FIGS. 1–3). Alternatively, the pin 23a can be coupled to other types of appliances such as the appliances mentioned above.

The body 21a has a post that extends through the hole in the distal end portion of the upper link 12 as well as through an opening in an annular cover 25a. The outer end of that post is peened over to form an enlarged head that retains the cover 25a in place. Optionally, the cover 25a is brazed or welded to the post of the body 21a.

The device 10 also has a lower pivotal connector 24 that is pivotally coupled to the distal end portion of the lower link 14. The lower connector 24 includes a pivot body 26 and a pin 28 that are shown in detail in FIGS. 6–7. The pin 28 extends through a mesiodistally extending passage 31 in the body 26 and also through a mesiodistally extending passage of an appliance that is affixed to one of the teeth of the patient's lower jaw such as the first molar tooth.

The connector 24 optionally includes a cover 25 having a central opening. (The cover has been omitted in FIG. 6 to show inner details of the connector 24). The body 26 has a central post 27 that extends through a hole of the distal end portion of the lower link 14 as well as through the opening in the cover 25. The outer end of the post 27 is peened over to form an enlarged head that secures the cover 25 snugly against the body 26 and captures the distal end portion of the lower link 14 in the space between the cover 25 and a lingual wall section of the body 26.

In the example shown in FIGS. 1–3, the pin 28 extends through an appliance 30 known as a lip bumper tube. The appliance 30 is affixed to a band that, in turn, encircles and is connected to one of the teeth of the patient's lower jaw. Preferably, but not necessarily, the encircled tooth is a lower first molar tooth. However, other types of appliances may be used, and may be mounted on or connected to teeth other than first molar teeth.

Figure 6:
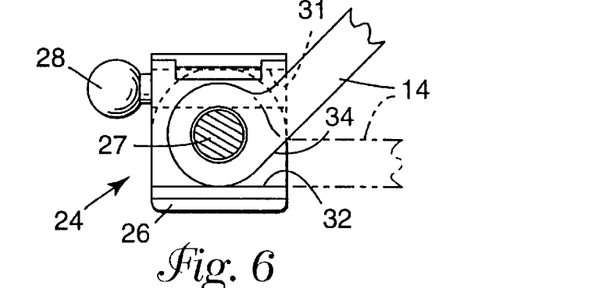
FIG. 6 is an enlarged fragmentary side view in partial section showing a lower pivotal connector of the device of FIGS. 1–3.
Figure 7:
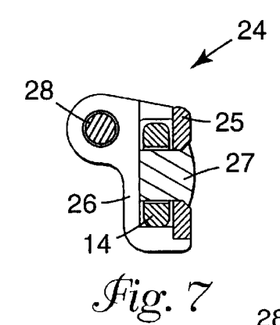
FIG. 7 is an enlarged end cross-sectional view of the lower pivotal connector illustrated in FIG. 6.

Preferably, one of the connectors 18, 24 includes a stop for limiting swinging movement of the links 12, 14 when the patient's upper and lower jaws are closed. In the illustrated embodiment, the body 26 of the lower connector 24 includes a stop 32 that comprises a shoulder which extends in a plane generally parallel, and preferably parallel, to the patient's occlusal plane. When the patient's jaws are closed, the stop 32 engages a lower surface section 34 of the distal end portion of the lower link 14, and prevents further swinging movement of the lower link 14 in a clockwise direction viewing FIG. 1 from its illustrated orientation. In FIG. 6, phantom lines indicate the lowermost orientation of the link 14 as it appears when the section 34 engages the stop 32.

The device 10 is installed by moving the outer end of the pin 28 in a mesial direction through the passage in the body 26 and then through the distal opening of the passageway 31. Next, the outer end of the pin 28 is bent with a pliers or other tool in order to cinch the lower connector 24 to the appliance 30. If desired, spacers (such as a short section of tubing) could be placed on the pin 28 between the body 28 and the appliance 30 to provide a proper fit and to also limit axial play. The mesial section 21 of the upper connector 18 is then inserted through the distal end of the tubular opening of the buccal tube 22 and moved in a mesial direction. Next, the patient postures the lower jaw in the orientation desired by the orthodontist while the jaws are closed. The mesial tip of the mesial section 21 is then bent in an arc in order to secure the upper connector 18 to the buccal tube 22.

Once installed, the device 10 allows the jaws to be opened without undue hindrance. Each time that the jaws are closed, the links 12, 14 serve to reposition the jaws to their relative orientations as occurred when the device 10 was initially installed and the connectors 18, 24 were secured to the appliances 22, 30. The rigidity of the links 12, 14 ensures that the desired jaw relationship is achieved each time that the jaws are closed.

As another option, one or both of the rigid links 12, 14 could be replaced with a deformable link or with a telescoping, spring-biased assembly. Such deformable links or telescoping assemblies can serve to limit the total amount of force supplied by the device 10 when the jaws are closed, a particular advantage when it is important to reduce the maximum possible force applied to either of the appliances 22, 30. For example, a deformable link or link assembly may be constructed similar to the devices described in U.S. Pat. No. 4,708,646, 5,352,116, 5,435,721 and 5,651,672. Deformable or telescoping, spring-biased assemblies may also be desired in instances where a somewhat yieldable force is desired when the patient's jaws are closed. As still another option, the connectors 18, 24 may be made of a deformable material or may be coupled to appliances by one or more elastomeric members to provide yielding, force-limiting structure. For example, the connectors 18, 24 may be connected by an elastic or flexible coupler to a pin or auxiliary archwire that, in turn, is connected to a buccal tube, bracket or principal archwire.

The links 12, 14 may be provided in different lengths to enable the practitioner to select an optimal size for any given patient. Alternatively, one or both of the links 12, 14 may have a variable effective length. For example, one or both of the links 12, 14 may comprise an adjustable threaded rod and cylinder assembly. Alternatively, a force-limiting link as described in the preceding paragraph could have adjustable structure to vary its effective length.

Preferably, the mesial section 21 of the connector 18 freely pivots about its longitudinal axis. Additionally, the body 26 and/or the pin 28 freely pivot about the longitudinal axis of the pin 28 relative to the appliance 30. Such pivotal movements facilitate side-to-side movement or lateral excursion of the lower jaw relative to the upper jaw. Preferably, the mesial section 21 and the pin 28 have a cylindrical configuration in order to enhance such pivotal movement. The distal sections of the pin connector 18 and the central axis of the post 27 extend parallel to the central axis of the shank 11 as well as to the condylar or hinge axis of the patient's jaws.

Preferably, at least one of the links 12, 14 has an offset section to reduce the likelihood of pinching soft tissue of the patient's cheeks as the jaws are closed. In the embodiment illustrated in the drawings, the lower link 14 has an offset section 36 near its mesial end portion. The offset section 36 functions to increase the angle between the mesial portions of the links 12, 14 in order to avoid a scissors-like effect of the links in areas near the pivot 16.

As shown in FIG. 1, the offset section 36, the stop 32 and the lower surface section 34 are arranged to sustain the pivot 16 in a position between the brackets mounted on the patient's upper dental arch and the patient's lower dental arch when the patient's jaws are closed, and more preferably sustain the pivot 16 in a position lying in or very near the occlusal plane of the patient. Such construction is an advantage in that the pivot 16 is unlikely to impinge the patient's oral tissues when the device 10 is in use, and particularly is unlikely to impinge the patient's gingiva (i.e. the gums). Location of the pivot 16 in or near the occlusal plane during closure of the jaws also tends to apply the substantial majority of the corrective forces to both of the jaws in a direction closely parallel to the occlusal plane, which is believed to improve the effectiveness of the device 10 during treatment.

For purposes of illustration, FIGS. 1–3 also show a series of brackets 38 that are mounted on teeth of the patient's upper jaw and a series of brackets 40 that are mounted on teeth of the patient's lower jaw as they might appear during orthodontic treatment. An upper archwire 42 is placed in slots of the upper brackets 38 and extends through a passage in the buccal tube appliance 22. A lower archwire 44 extends through slots of the lower brackets 40 and is received in a passage of the lower appliance 30.

The mandibular repositioning device 10 according to the invention is normally used in pairs. The device 10 illustrated in FIGS. 1-3 is shown as mounted on the right side of the patient's jaws. A somewhat similar device that is a mirror image to the device 10 is mounted on the left side of the patient's jaws and is received in molar appliances similar to the appliances 22, 30.

The rigid links 12, 14 are an advantage in comparison to the telescoping tube assemblies described above in that the links 12, 14 are relatively simple to manufacture and assemble. Moreover, the links, 12, 14 remain secured together by the pivot 16 even when the jaws are fully opened. In some of the telescoping tube assemblies described above, the piston may unintentionally withdraw and separate from the cylinder when the patient's jaws are fully opened, requiring careful reassembly before jaw repositioning treatment can be resumed.

Figure 8:
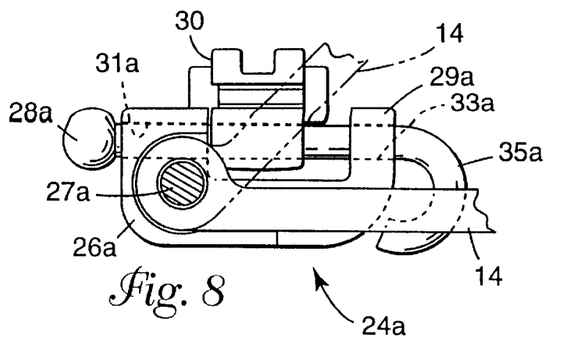
FIG. 8 is an enlarged fragmentary side view in partial section of an alternative lower pivotal connector according to an alternate embodiment of the invention.

A lower pivotal connector 24a as shown in FIG. 8 represents an alternative to the connector 24 illustrated in FIGS. 1–3 and 6–7. The connector 24a is somewhat similar to the connector 24 in that the connector 24a includes a body 26a and a pin 28a, and the body 26a has a post 27a that extends through the hole in the distal end portion of the lower link 14. The outer end of the post 27a has a peened-over head that functions to secure a cover (not shown) to the body 26a and capture the lower link 14 in a pivotally coupled relationship relative to the body 26a.

However the body 26a includes a mesially-extending support section 29a that is located on a lingual side of the path of travel of the lower link 14. The support section 29a includes an outer, occlusally-extending tip having a cylindrical passage 33a that is aligned with the passage 31a extending through the body 26a near the post 27a. As shown in FIG. 8, the pin 28a extends not only through the passage 31a and the passage of the appliance 30, but also through the passage 33a.

The dual, spaced-apart, aligned passages 31a, 33a are an advantage because better support is provided for the body 26a and cantilever-type stresses are reduced. Such construction enables the pin 28a to better resist bending forces that might otherwise deform or fracture the pin 28a and reduce the possibility of unintentional detachment of the body 26a from the appliance 30 during use. An outer, mesial tip 35a of the pin 28a is bent in an arc as shown in FIG. 8 during installation to secure the connector 24a to the appliance 30, but can be readily straightened when desired by a pliers or other hand tool for removal from the passages 31a, 33a and from the passage in the appliance 30 in order to uncouple the connector 24a from the appliance 30.

Figure 9:
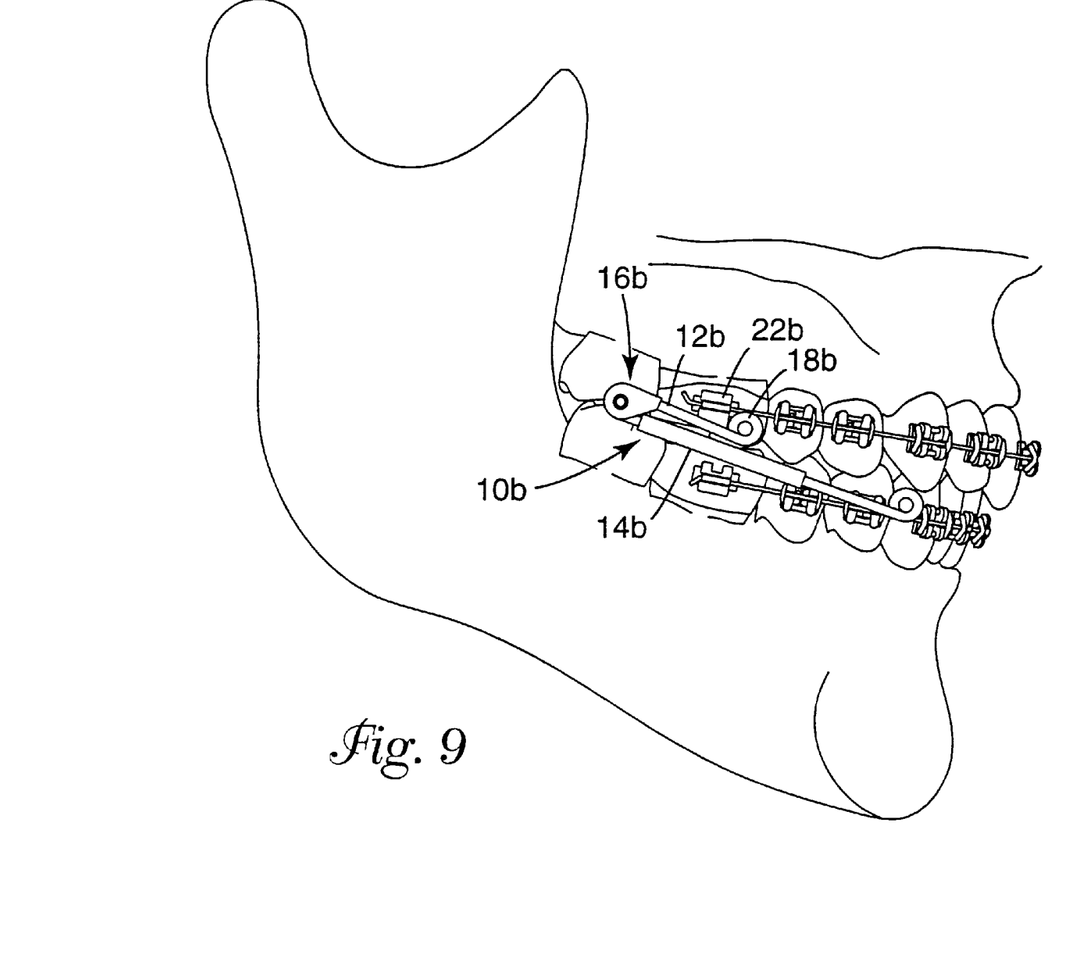
FIG. 9 is a view somewhat similar to FIG. 1 except that a mandibular repositioning device according to yet another embodiment of the invention is illustrated.
Figure 10:
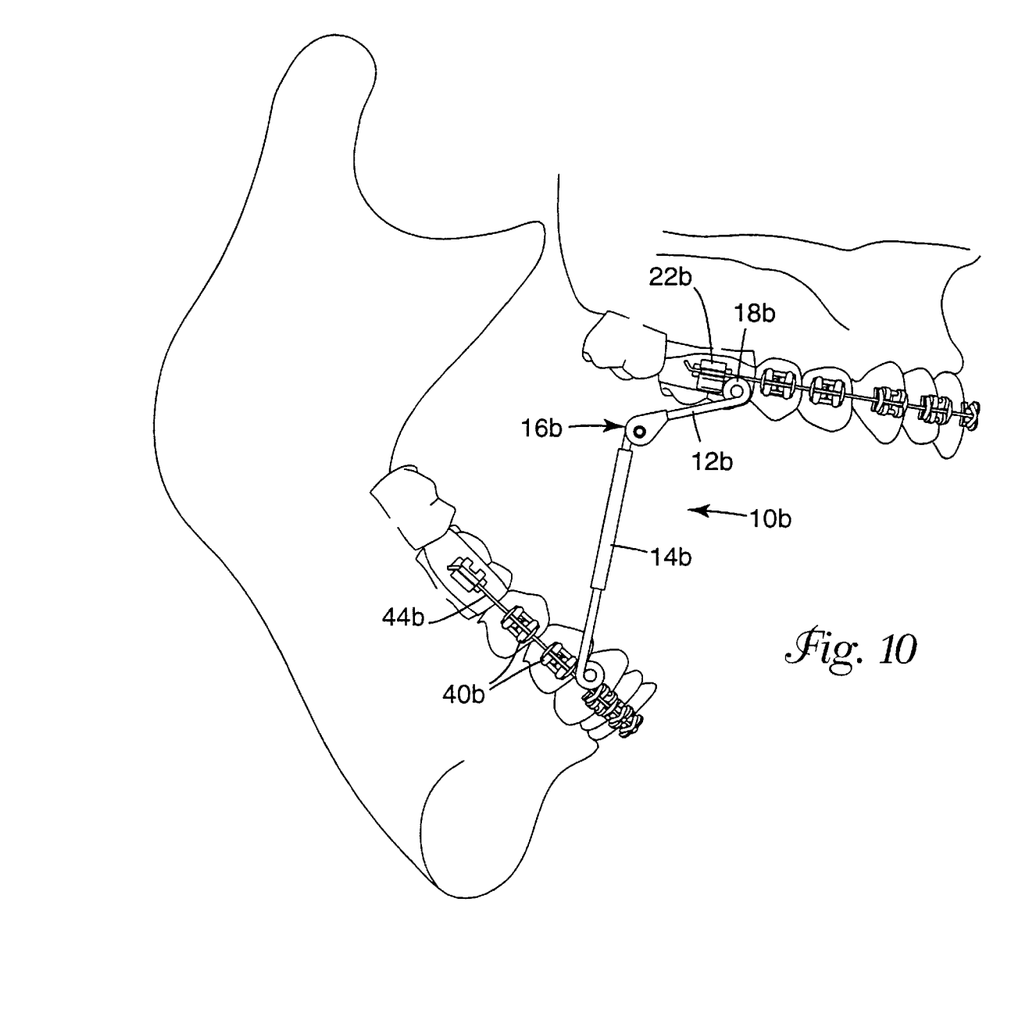
FIG. 10 is a view somewhat similar to FIG. 9 except that the patient's jaws have been opened.

Another embodiment of the invention is shown in FIGS. 9 and 10, wherein a device 10b has an upper link 12b and a lower link 14b. A pivot 16b connects a distal end of the upper link 12b to a distal end of the lower link 14b.

The device 10b includes an upper pivotal connector 18b that is somewhat similar to the "L"-shaped connector 18 described above but reversed in orientation. The upper connector 18b pivotally connects the mesial end of the upper link 12b to a molar appliance 22b. The upper connector 18b extends in a distal direction through the appliance 22b. Preferably, the connector 18b includes a stop to limit swinging movement of the links 12b, 14b when the jaws are closed so that that pivot 16b is located on or near the patient's occlusal plane.

A mesial end of the lower link 14b is pivotally coupled to the patient's lower dental arch. As one option, the pivotal coupling is connected to a lower archwire 44b that extends through lower brackets 40b. As another option, the mesial end of the lower link 14b is pivotally coupled to an auxiliary archwire (not shown) that extends along the patient's lower dental arch. As yet another option, the mesial end of the lower link 14b may be pivotally coupled to a cantilever device such as is described in various forms in U.S. Pat. No. 5,718,576, which is incorporated by reference.

Optionally, at least one of the links 12b, 14b of the device 10b is variable in effective length such as by use of threaded rod and cylinder assemblies. Moreover, one or both of the links 12b, 14b could comprise a deformable or flexible members or a telescoping assembly as mentioned above. In the embodiment shown in FIGS. 9 and 10, the lower link 14b is comprised of a telescoping assembly that includes a mesially-oriented piston and a distally-oriented cylinder. Optionally, the telescoping assembly includes an internal or external coil spring to provide a force that is yieldable as the jaws are closed.

The various components of the devices 10, 10a, 10b are preferably made of a corrosion-resistant material. A suitable material is stainless steel such as AISI 300 series types (including nos. 302 or 304), although other materials may also be employed.

Moreover, it may be apparent to those skilled in the art that a number of modifications and additions may be made to the devices described above without departing from the spirit of the invention. Accordingly, the invention should not be deemed limited to the presently preferred embodiments that are set out in detail above, but instead only by a fair scope of the claims that follow along with their equivalents.

I claim:

1. A mandibular repositioning device comprising:
   an upper link having a mesial end portion and a distal end portion;
   a lower link having a mesial end portion and a distal end portion;
   a pivot connecting the mesial end portion of the upper link to the mesial end portion of the lower link;
   an upper connector pivotally coupled to the distal end portion of the upper link; and
   a lower connector pivotally coupled to the distal end portion of the lower link, wherein the upper connector and the lower connector each have a configuration for partial reception into passages of an upper molar appliance and a lower molar appliance respectively, wherein the upper link and the lower link each have a length sufficient to urge one jaw forwardly relative to the other jaw when the jaws are closed, wherein the pivot is located mesially of the upper connector and the lower connector when the jaws are closed, and wherein the upper link and the lower link are each relatively rigid and have fixed effective lengths in use.

2. A mandibular repositioning device according to claim 1, wherein the upper connector is pivotally coupled to the distal end of the upper link for swinging movement of the upper link about an axis that is parallel to the pivotal axis of the pivot connecting the mesial end portion of the upper link to the mesial end portion of the lower link, and wherein the lower connector is pivotally coupled to the distal end of the lower link for swinging movement of the lower link in an arc about an axis that is parallel to the pivotal axis of the pivot connecting the mesial end portion of the upper link to the mesial end portion of the lower link.

3. A mandibular repositioning device according to claim 1, wherein the pivot extends in a reference plane that lies near the occlusal plane of the patient when the patient's jaws are closed.

4. A mandibular repositioning device according to claim 1, wherein the pivot extends in a reference plane that is located aroximately midway between the upper molar appliance and the lower molar appliance when the jaws are closed.

5. A mandibular repositioning device according to claim 1 and including a stop for limiting pivotal movement of at least one of the links.

6. A mandibular repositioning device according to claim 5, wherein one of the connectors includes the stop.

7. A mandibular repositioning device according to claim 1, wherein at least one of the links has a variable effective length.

8. A mandibular repositioning device according to claim 7, wherein each link having a variable effective length is flexible and assumes a bowed configuration when the patient's jaws are closed.

9. A mandibular repositioning device according to claim 7, wherein at least one of the links includes a piston and cylinder assembly.

10. A mandibular repositioning device according to claim 9, wherein the piston and cylinder assembly includes a coil spring for urging the piston in an outwardly direction relative to the cylinder.

11. A mandibular repositioning device according to claim 1, wherein at least one of the links includes an offset portion.

12. A mandibular repositioning device comprising:
    an upper link having a mesial end portion and a distal end portion;
    a lower link having a mesial end portion and a distal end portion;
    a pivot connecting the mesial end portion of the upper link to the mesial end portion of the lower links;
    an upper connector pivotally coupled to the distal end portion of the upper link; and
    a lower connector pivotally coupled to the distal end portion of the lower link, wherein the upper connector and the lower connector each have a configuration for partial reception into passages of an upper molar appliance and a lower molar appliance respectively, wherein the upper link and the lower link each have a length sufficient to urge one jaw forwardly relative to the other jaw when the jaws are closed, wherein the pivot is located mesially of the upper connector and the lower connector when the jaws are closed, wherein the upper connector is pivotally coupled to the distal end of the upper link for swinging movement of the upper link about an axis that is parallel to the pivotal axis of the pivot connecting the mesial end portion of the upper link to the mesial end portion of the lower link, wherein the lower connector is pivotally coupled to the distal end of the lower link for swinging movement of the lower link in an arc about an axis that is parallel to the pivotal axis of the pivot connecting the mesial end portion of the upper link to the mesial end portion of the lower link, and wherein at least one of the connectors has an overall, generally "L"-shaped configuration.

13. A mandibular repositioning device according to claim 12, wherein each connector having the "L"-shaped configuration is adapted for pivotal movement within passages of molar appliances.

14. A mandibular repositioning device according to claim 12, wherein the upper link and the lower link are each relatively rigid and have fixed effective lengths in use.

15. A mandibular repositioning device consisting essentially of an upper link, an upper connector pivotally connected to the upper link for coupling the upper link to an appliance fixed to a tooth of the patient's upper jaw, a lower link, a lower connector pivotally coupled to the lower link for coupling the lower link to an appliance fixed to a tooth of the patient's lower jaw, and a pivot interconnecting the upper link and the lower link and remote from the upper connector and the lower connector, wherein the upper link and the lower link are each relatively rigid and have a fixed effective length in use.

16. A mandibular repositioning device according to claim 15, and including a stop for limiting pivotal movement of at least one of the links.

17. A mandibular repositioning device according to claim 16, wherein one of the connectors includes the stop.

18. A mandibular repositioning device according to claim 15, wherein the pivot extends in a reference plane that is located between the upper molar appliance and the lower molar appliance.

19. A mandibular repositioning device according to claim 15, wherein the pivot extends in a reference plane that lies near the occlusal plane of the patient when the patient's jaws are closed.

20. A mandibular repositioning device according to claim 15, wherein the upper connector is pivotally coupled to the distal end of the upper link for swinging movement of the upper link about an axis that is parallel to the pivotal axis of the pivot connecting the mesial end portion of the upper link to the mesial end portion of the lower link, and wherein the lower connector is pivotally coupled to the distal end of the lower link for swinging movement of the lower link in an arc about an axis that is parallel to the pivotal axis of the pivot connecting the mesial end portion of the upper link to the mesial end portion of the lower link.

21. A mandibular repositioning device according to claim 15, wherein at least one of the connectors has an overall, generally "L"-shaped configuration.

22. A mandibular repositioning device according to claim 15, wherein each connector having the "L"-shaped configuration is adapted for pivotal movement within passages of molar appliances.

23. A mandibular repositioning device according to claim 15, wherein at least one of the links includes an offset portion.

* * * * *

UNITED STATES PATENT AND TRADEMARK OFFICE
CERTIFICATE OF CORRECTION

PATENT NO.: 5,980,247
DATED: November 9, 1999
INVENTOR(S): James D. Cleary

It is certified that error appears in the above-identified patent and that said Letters Patent is hereby corrected as shown below:

Column 9, line 53 "aroximately" should read ---approximately---.

Column 10, line 16 "links" should read ---link---.

Signed and Sealed this

First Day of May, 2001

Attest:

NICHOLAS P. GODICI

Attesting Officer      Acting Director of the United States Patent and Trademark Office